(12) United States Patent
Wang et al.

(10) Patent No.: US 10,779,793 B1
(45) Date of Patent: Sep. 22, 2020

(54) X-RAY DETECTOR POSE ESTIMATION IN MEDICAL IMAGING

(71) Applicant: Siemens Healthcare GmbH, Erlangen (DE)

(72) Inventors: Rui Wang, Chapel Hill, NC (US);
Yao-jen Chang, Princeton, NJ (US);
Vivek Kumar Singh, Princeton, NJ (US); Birgi Tamersoy, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 30 days.

(21) Appl. No.: 16/292,716

(22) Filed: Mar. 5, 2019

(51) Int. Cl.
*A61B 6/00* (2006.01)
*G06T 7/73* (2017.01)

(52) U.S. Cl.
CPC ............... *A61B 6/547* (2013.01); *G06T 7/74* (2017.01); *G06T 2207/10048* (2013.01); *G06T 2207/20081* (2013.01); *G06T 2207/20084* (2013.01); *G06T 2207/30204* (2013.01)

(58) Field of Classification Search
CPC . A61B 6/547; G06T 7/73; G06T 2207/10081; G06T 2207/20081; G06T 2207/30204
See application file for complete search history.

(56) References Cited

U.S. PATENT DOCUMENTS

| | | | |
|---|---|---|---|
| 2002/0065461 A1* | 5/2002 | Cosman | A61B 90/16 600/426 |
| 2003/0194056 A1* | 10/2003 | Spahn | A61B 6/08 378/205 |
| 2009/0278702 A1* | 11/2009 | Graumann | A61B 34/20 340/686.2 |
| 2010/0239070 A1 | 9/2010 | Mohr | |
| 2017/0010089 A1 | 1/2017 | Jung | |
| 2018/0092619 A1* | 4/2018 | Gu | A61B 6/4405 |
| 2018/0235566 A1 | 8/2018 | Tamersoy | |

* cited by examiner

*Primary Examiner* — David P Porta
*Assistant Examiner* — Fani Boosalis

(57) ABSTRACT

For x-ray detector pose estimation, a machine-learned model is used to estimate locations of markers, including occluded or other non-visible markers, from an image. The locations of the markers, including the non-visible markers are used to determine the pose of the X-ray detector for aligning an X-ray tube with the X-ray detector.

16 Claims, 4 Drawing Sheets

X-RAY DETECTOR POSE ESTIMATION IN MEDICAL IMAGING

BACKGROUND

The present embodiments relate to X-ray detector pose estimation for X-ray imaging. In robotic X-ray systems, the X-ray source and detector have several degrees-of-freedom (DOF). For example, the detector may be a mobile plate positionable in various locations and/or orientations. The x-ray source connects to a robotic arm to allow positioning generally orthogonal to the detector for x-ray imaging. The freedom of positioning provides an advantage in terms of flexibility in imaging the patient. Such systems enable high quality X-ray examinations to be carried out for more specific regions of interests and for a wider range of patients (e.g. in cases of serious trauma).

In order to acquire high quality images, the X-ray source, the region-of-interest, and the X-ray detector should be well aligned. The better the alignment, the higher the quality of the X-ray image will be. This alignment is performed in two steps: positioning the X-ray detector with respect to the region-of-interest of the patient, and then aligning the X-ray source with respect to the X-ray detector. Conventionally, an operator performs the detector positioning and X-ray source alignment manually. Because the alignment is performed manually, the quality of the alignment is not consistent, difficult to reproduce every time, and time consuming.

U.S. Published Application No. 2018/0235566 teaches automatic alignment by locating markers on the detector. The pose of the X-ray detector is determined from the located markers in a process providing for marker detection, detector plane estimation, and then detector position estimation based on an image from a camera. The markers are detected using hand-crafted filters with different sizes and a Hough transform-based approach. Each marker is then classified to match with a pre-defined template detector. After the markers are detected, a region growing algorithm is applied on a depth image to obtain a detector plane. Then, the pose of the X-ray detector position is estimated based on the point-correspondence to the template. However, in some cases, some or many of the markers are occluded, resulting in less accuracy in pose prediction. The approach may also have difficulty handling large distance variation of the detector relative to the camera.

SUMMARY

Systems, methods, and instructions on computer readable media are provided for x-ray detector pose estimation. A machine-learned model is used to estimate locations of markers, including occluded or other non-visible markers, from an image. The locations of the markers, including the non-visible markers are used to determine the pose of the X-ray detector for aligning an X-ray tube with the X-ray detector.

In a first aspect, a method is provided for estimating X-ray detector pose. An image of the X-ray detector is captured. Locations of visible and occluded markers on the X-ray detector are identified from the image by a machine-learned detector. The X-ray detector pose of the X-ray detector is determined from the locations of the visible and occluded markers. An X-ray tube is positioned based on the X-ray detector pose. A patient is x-ray imaged with the X-ray tube as positioned and the X-ray detector.

The image does not show the occluded markers due to an intervening object, such as a patient. The image may not show markers that are outside of the field of view of the camera. The locations of the occluded markers and/or out-of-view markers not shown by the image are still identified.

In various embodiments, the image may be captured as an infrared (IR) image. A camera may be fixedly connected and moveable with the X-ray tube. Assuming the X-ray detector is partially visible inside of the camera's field of view, the captured image may be padded to virtually enlarge the field of view such that the padded image is more likely to include the entirety of the X-ray detector.

The machine-learned detector may be of various types of machine-learned models, such as a deep neural network trained with deep learning. The network structure of the machine-learned detector may be a single network or a sequence of two or more networks. For example, a first of the two or more networks is trained to localize the X-ray detector in the image in a coarse level, and a second of the two or more networks is trained to locate the visible, occluded and/or other out-of-view markers in response to the localization output by the first of the two or more networks. The second of the two or more networks may be trained to locate in response to an input of the image cropped based on the localization output of the first network. A third of the two or more networks may be trained to refine positions of the visible, occluded and/or other out-of-view markers output by the second of the two or more networks where the refined positions are the identified locations.

The identification of the locations may include generating a heatmap of the locations. The heatmap provides probabilistic indication of possible locations for each marker.

In one embodiment, the X-ray detector pose is determined with homography. A position and orientation in three dimensions of the X-ray detector pose is determined from the geometrical relationship of the markers to each other as viewed by the camera.

In a second aspect, an X-ray imaging system is provided. An X-ray source connects to a movable arm. A camera connects to the X-ray source or moveable arm to be movable with the X-ray source. An X-ray detector is moveable independent of the movable arm. An image processor is configured to determine a position, orientation, or position and orientation of the X-ray detector relative to the X-ray source based on markers shown by the camera and markers not shown by the camera. The markers not shown by the camera are located by a machine-learned network.

In one embodiment, the moveable arm is a robotic arm, and the X-ray detector is a flat panel detector. The camera is an infrared camera. The markers are reflective for ease of detection by the camera.

In one embodiment, the camera is a color camera. The markers are painted with distinguishable color compared to the X-ray detector, such that the markers may be easily detected by the camera.

A display configured to display an X-ray image of the patient may be provided. The X-ray image is acquired based on positioning of the X-ray source relative to the position, orientation, or position and orientation determined by the image processor.

In one embodiment, the image processor is configured to apply the machine-learned network to an image from the camera. The machine-learned network outputs the markers not shown by the camera in response to the application.

In a third aspect, a method is provided for locating markers on an X-ray detector. A region including a detector with markers and a patient is imaged with a camera. The patient intervenes between the camera and at least some of the markers. A machine-learned model determines, from the imaging, locations of the markers including the at least some of the markers for which the patient is intervening.

In a further embodiment, the imaging is with infrared. The markers are infrared-reflective markers. A position and orientation of the X-ray detector is determined based on the locations, and an X-ray source is positioned with a robotic arm based on the position and orientation of the X-ray detector.

In another embodiment, the region is a padded image with a processing-created enlarged field of view of the camera. The machine-learned model is a machine-learned network including a first image-to-image network trained to locate the detector in the field of view of the camera and a second image-to-image network trained to determine the locations from the imaging cropped based on the located detector from the first image-to-image network.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

FIG. 2 is a detailed view of the mobile X-ray detector in FIG. 1.

DETAILED DESCRIPTION OF EMBODIMENTS

X-ray detector pose estimation is provided by a machine-learned model, such as a deep neural network trained with deep learning methods. Deep or other machine learning-based technique is used to automatically compute the transformation to place the X-ray tube at an ideal imaging location. The machine is trained for landmark detection. In one embodiment, several dedicated convolutional neural networks are trained to estimate visible markers and predict the position of occluded and out-of-view markers. Occluded and out-of-view markers are robustly estimated, making the pose estimation with very few visible markers more accurate.

This learning-based landmark detection does not require any hand-crafted filters and achieves better detection accuracy and generality as compared to the approach of U.S. Published Application No. 2018/0235566. No explicit marker classification or detection is required. Since the machine learning is data driven, the resulting machine-learned model may adapt to any kind of detector, detector occlusion, detector marker placement, and detector positioning given appropriate training data.

Figure 1A:
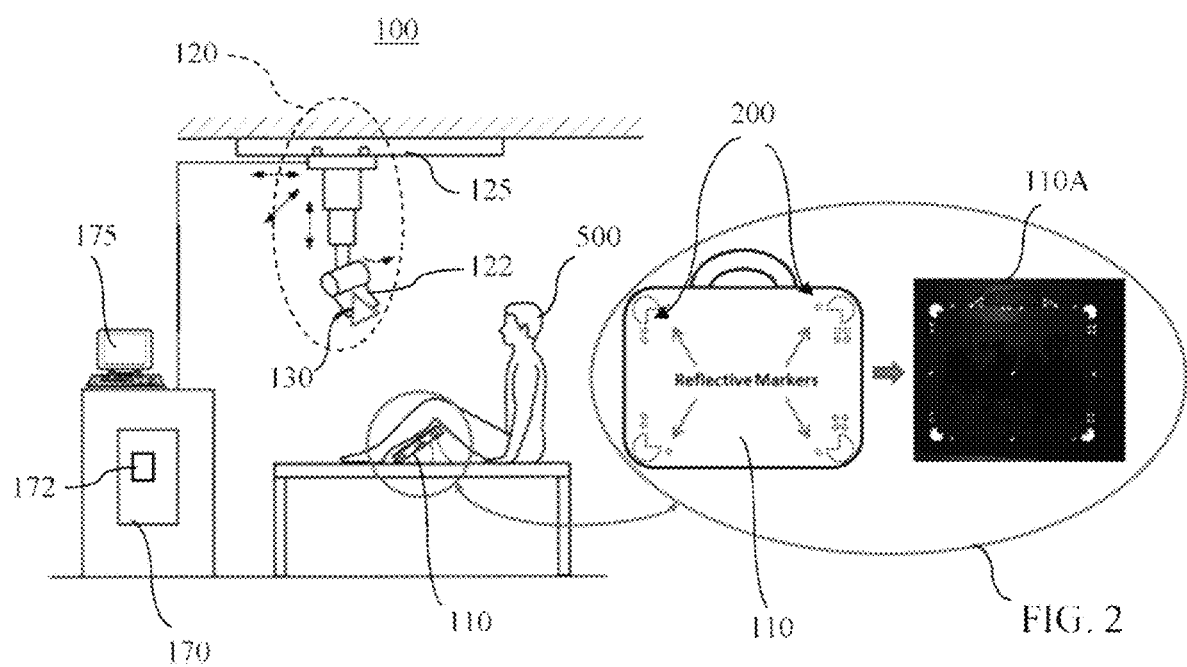
FIG. 1A shows an X-ray system utilizing a mobile X-ray detector according to various embodiments.

FIG. 1A shows an X-ray imaging system 100. The X-ray imaging system 100 provides for automatic alignment of the X-ray source 122 and the mobile X-ray detector 110. The automatic alignment utilizes a camera 130 provided on the positionable X-ray source 122 and the mobile X-ray detector 110 having passive markers 200 placed thereon. A machine-learned model implemented by the controller 170 determines a position of the X-ray detector 110 from an image of the camera 130 even where some or many of the markers 200 are out-of-view (e.g., occluded or outside the field of view of the camera) in the image.

One embodiment of such X-ray system 100 includes an X-ray tube robot system 120, the positionable X-ray source 122, an X-ray source base 125, the camera 130 mounted on or by the X-ray source 122, the mobile X-ray detector 110, and the system controller 170. Additional, different, or fewer components may be provided, such as including a computer network for remote image processing and/or control by computer, server, or workstation forming the system controller 170.

The X-ray system 100 is for training, such as using images from a memory 177 and/or the camera 130 and a corresponding ground truth as input samples. Alternatively, the X-ray system 100 is for application of the machine-learned model trained to detect locations of the markers 200.

The X-ray tube robot system 120 is configured and adapted to be driven by the system controller 170 for articulating the positionable X-ray source 122 into any desired position to align the X-ray source 122 with the mobile X-ray detector 110. For example, the X-ray tube robot system 120 is a robotic arm on which the X-ray source 122 is arranged. Such a robotic arm allows a particularly variable adjustability of the X-ray source 122. Alternatively, the X-ray tube robot system 120 is a telescoping arm that is hung from overhead tracks. Other robotic arms may be used. In other embodiments, a manually moveable support structure or arm is provided for the X-ray source 122. The user is guided to position based one or more images on the display 175.

The X-ray source 122 is an X-ray tube. Multiple X-ray sources 122 may be provided, such as for a dual energy X-ray imager.

The X-ray source 122 is fixedly connected to the movable arm, such as the robot system 120. The connection may be removable, such as by undoing a latch, removing a housing, and/or removing bolts. The X-ray source 122 is connected so that moving the end or other part of the robot system 120 moves the X-ray source 122. The X-ray source 122 is movable by the movable arm (e.g., robotic arm) in one or more degrees of translation freedom with or without one or more degrees of rotation freedom.

The camera 130 may be an optical camera. The camera 130 images in the visible light spectrum. The visible light camera 130 produces an RGB (Red, Green, Blue) digital image.

In one embodiment, the camera 130 is a depth sensing camera (e.g., three-dimensional (3D) or RGBD camera). The depth sensing may allow the camera 130 to determine a depth from the camera 130 to any of the visible markers 200. The digital image data obtained from such camera 130 is typically referred to as an RGBD (RGB+Depth) image, which includes an RGB image, in which each pixel has an RGB value and a depth (or distance) value.

In another embodiment, the camera 130 is an infrared (IR)-based camera, with or without a depth sensor. The infrared camera captures images of passive markers 200, which are IR reflective markers 200 that have strong response on the infra-red light projected onto the markers. The IR-based camera 130 produces an IR digital image in which each pixel has an IR value. The digital image data obtained from such IR-based camera 130 is an IR image. With depth sensing, an IRD image is obtained.

Other cameras may be used. A camera or cameras that operate in two or more modes (e.g., visible spectrum and IR) may be used. A camera with two or more sensors in either visible spectrum or IR may be used. Two or more cameras 130 may be provided. The camera 130 position and optics are calibrated relative to the X-ray source 122 and/or the base 125 of the X-ray system 100.

The camera 130 attaches to an appropriate location on the X-ray source 122 and/or the robot system 120. In some embodiments, the camera 130 is attached to a rear side of the X-ray source 122. The camera 130 is fixedly connected to the movable arm, such as the robot system 120. The connection may be removable, such as by undoing a latch, removing a housing, and/or removing bolts. The camera 130 is connected so that moving the end or other part of the robot system 120 moves the camera 130 with the X-ray source 122. The camera 130 is movable by the movable arm (e.g., robotic arm) in one or more degrees of translation freedom with or without one or more degrees of rotation freedom.

The X-ray detector 110 is a flat-panel detector for recording high-quality X-ray images. In some embodiments, the X-ray detector 110 is wireless and is configured with a transceiver for wireless communication with the system controller 170, for example, for transmitting the acquired X-ray images. In some embodiments, the X-ray detector 110 has a wired connection to the X-ray system 100 and so quick and error-free communication between the X-ray detector 100 and a component of the X-ray system 100 differing therefrom is ensured.

The detector 110 is movable independent of the moveable arm or robot system 120. The detector 110 is movable independent of the X-ray source 122. The X-ray detector 110 may be manually positioned anywhere about the patient 500 by an X-ray technician in order to record X-ray images of a region of interest on the patient 500. In the example illustration of FIG. 1A, the mobile X-ray detector 110 is positioned for an X-ray examination of a patient 500's femur region. The detector 110 is a movable detector 110, such as being free of connection or releasably connected to the rest of the X-ray system 100. The mobile detector 110 may be placed in a drawer in or below the patient bed. The mobile detector 110 may be placed in a bracket or connected to a shim or other positioning apparatus. The mobile detector 110 may be released and moved to other locations or moved to other locations while attached to a position apparatus (e.g., a wedge holder). The mobile detector 110 may have any number of degrees of freedom, such as a being a plate or flat panel that may be positioned on top of the patient bed in any arbitrary position and/or orientation. Alternatively, the detector 110 mounts to or is connected fixedly with a manual armature or an automatic robotic arm, such as being part of a C-arm with the X-ray source 122 on the end of the robot system 120. The connection may allow for changeable translation and/or orientation of the detector 110 relative to the X-ray source 122.

The detector 110 has a plurality of passive markers 200 placed at designated points on one or more surfaces of the X-ray detector 110. In one embodiment, the markers 200 are on a top surface or a surface that faces the X-ray source 122 in use. The marker placement allows the camera to see or image at least some of the markers 200.

The plurality of passive markers 200 are provided in shapes and patterns that may uniquely identify each of the corners of the mobile X-ray detector 110. Any combination of different shapes, patterns, and/or sizes are used. In some embodiments, the passive markers 200 include radial corner markers and smaller point markers as shown in FIG. 2. The larger radial corner markers are shaped for marking each of the four corners of the mobile X-ray detector 110. The smaller point markers are for the identification and validation of the larger radial corner markers such that the corners may be separately identified. In other embodiments, other shapes and configuration and placement of the passive markers 200 may be used. In yet other embodiments, the markers 200 have uniform shapes, such as being squares or rectangles of the same size with uniform or non-uniform placement on the detector 110.

In both the IR sensing and visible spectrum sensing, the passive markers 200 are used for detecting the mobile X-ray detector 110. The markers 200 are reflective and/or colored to be visible to the sensing. For visible spectrum imaging, the passive markers 200 have a color that is visually distinguishable from the color of the mobile X-ray detector's 110 surface, so that the camera 130 may see the passive markers 200 in the visible light spectrum. A marker with two or more colors may also be used. Contrasting colors between the markers 200 and the rest of the detector 110 are provided, such as black markers 200 on a beige or white housing of the detector 110. The markers 220 may be formed as an aesthetic element, such as an inset line or pattern.

For IR imaging, the IR reflective markers 200 may be color markers made to blend in with the color of the detector 110 such that the markers 200 are not so noticeable in the visible spectrum but are noticeable in the IR spectrum. FIG. 2 shows an IR image 110A in gray scale of the detector 110 where the markers 200 are lighter than the rest of the detector 110. The reflective markers 200 appear white because these reflective markers 200 reflect IR from the IR source back to the IR camera 130, and the background appears dark because the light background surface diffuses and/or absorbs IR.

The system controller 170 controls the overall operation of the X-ray system 100. For example, the system controller 170 is configured with appropriate hardware, firmware, and/or software to control the operation of the X-ray source 122, camera 130, robot system 120, and reading of the detector 110. For example, the controller 170 controls and interfaces with the camera 130 to capture one or more images, the positionable X-ray source 122 to generate X-rays, and the robot system 120 to move the X-ray source based on a determined position of the detector 110. The system controller 170 uses the acquired RGB and/or IR images to determine the pose in 3D of the mobile X-ray detector 110 to then position the X-ray source 122 and drive the X-ray image acquisition function of the X-ray system 100.

Figure 1B:
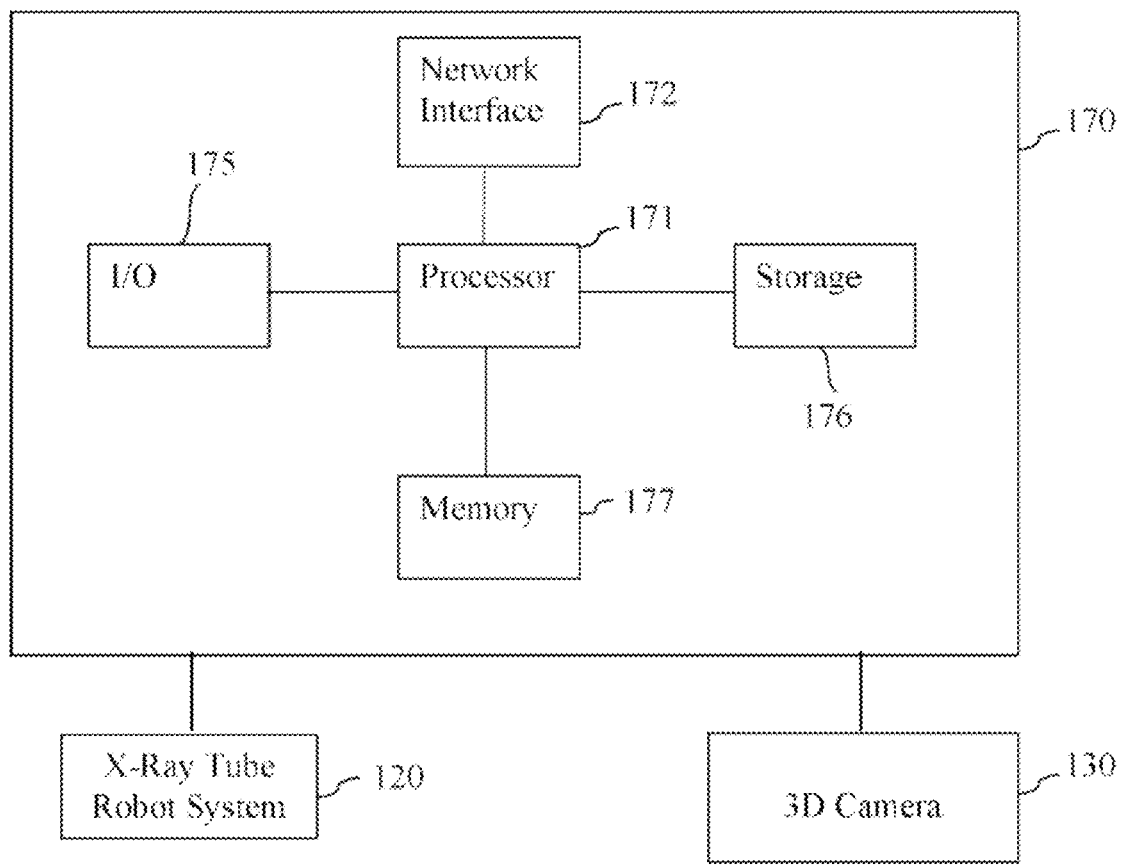
FIG. 1B is a high-level block diagram of one embodiment of a system controller for determining locations of occluded markers.

Referring to FIG. 1B, the system controller 170 may have a network interface 172 for communicating with other devices in the system 100 via a network and/or wired or wireless communications. For example, the network interface 172 is configured to carry out data transfer with the mobile X-ray detector 110 and the camera 130. Additionally, the X-ray system 100 has a user interfacing unit 175 (e.g., a touch and/or display screen, a keyboard, a mouse, etc.) for the X-ray technician to interface with the X-ray system. Such input/output devices 175 can be touch-screen interface, display, keyboard, mouse, speakers, buttons, etc. The system controller 170 may contain additional, different, or fewer components.

The system controller 170 may communicate with the X-ray tube robot system 120 to control the positioning and orientation of the X-ray source 122 and to control X-ray image acquisition by the mobile X-ray detector 110. X-ray images acquired by the X-ray detector 110 may be input to the system controller 170.

The system controller 170 includes the image processor 171. The image processor 171 may be separate from or part of the controller, which controls the overall operation of the system controller 170 by executing computer program instructions which define such operation. The image processor 171 is a control processor, general processor, digital signal processor, three-dimensional data processor, graphics processing unit, application specific integrated circuit, field programmable gate array, artificial intelligence processor, digital circuit, analog circuit, combinations thereof, or other now known or later developed device for image processing and/or application of a machine-learned model. The image processor 171 is a single device, a plurality of devices, or a network of devices. For more than one device, parallel or sequential division of processing may be used. Different devices making up the image processor 171 may perform different functions, such as one device applying the machine-learned network to locate markers and determine detector pose from the located markers and a separate device for controlling the robot system 120. In one embodiment, the image processor 171 is a control processor or other processor of the X-ray system 100. The image processor 171 operates pursuant to stored instructions, hardware, and/or firmware to perform various acts described herein.

The instructions, camera image, network definition, machine-learned model, outputs, and/or other information are stored in a non-transitory computer readable memory, such as the memory 177 or storage 176. The memory 177 and/or storage 176 are external storage devices, RAM, ROM, database, and/or local memories (e.g., solid state drive or hard drive). The same or different non-transitory computer readable media may be used for the instructions and other data. The memory 177 and/or storage 176 may be implemented using a database management system (DBMS) and residing on a memory, such as a hard disk, RAM, or removable media. Alternatively, the memory 177 is internal to the processor 171 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 177). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the way the present embodiments are programmed.

The image processor 171 is configured to train a machine learning architecture. Based on a user provided or other source of the network architecture and training data, the image processor 171 learns features for an encoder and a decoder or other network parts to train the network. The result of the training is a machine-learned model for identifying marker locations from an image of the camera 130. Alternatively or additionally, the image processor 171 is configured to apply a previously machine-learned model to identify marker locations from a camera image to align the X-ray source 122 for X-ray imaging of a patient 500 based on a pose of the detector 110 positioned for such imaging.

The associated X-ray examination workflow is as follows: position the patient 500 appropriately; position the mobile X-ray detector 110 with respect to the region-of-interest of the patient 500; acquire one or more images of the scene using the camera 130; compute the 6 DOF pose of the X-ray detector 110 using the image(s); automatically position the X-ray source 122 to a position that is in alignment with the mobile X-ray detector 110 based on the 6 DOF pose information on the mobile X-ray detector 110; and then record one or more X-ray images of the region-of-interest of the patient 500. A display device connected to the I/O 175 is configured to display an X-ray image of the patient 500 based on positioning of the X-ray source 122 relative to the position, orientation, or position and orientation of the detector 110 as determined by the image processor 171.

The system controller 170 is configured to perform the portions of the above-mentioned workflow after the mobile X-ray detector is positioned in place with respect to the region-of-interest. In preferred embodiments, the system controller 170 is configured to initiate the process when a single command is inputted via the system controller's operator input device 175. For example, the single command can be a voice command, a click of a key, a click of a mouse, a touch on a touch screen, etc. The rest of the workflow does not require any manual intervention from the X-ray technician and the resulting alignment between the X-ray detector and the X-ray source is much more accurate than the conventionally achieved alignment.

By detecting the plurality of passive markers 200 in the digital image provided by the camera 130, the system controller 170 uses this information to calculate the accurate position and orientation of the mobile X-ray detector 100 in the X-ray system 100 and then automatically aligns the positionable X-ray source 122 to the mobile X-ray detector 110. The system controller 170 accomplishes this by performing transformations between the coordinate system of the camera 130, the coordinate system of the X-ray base 125, and the coordinate system of the positionable X-ray source 122. The result is more accurate and repeatable alignment of the X-ray source 122 and the mobile X-ray detector 110 compared to the conventional manual alignment.

The position of the mobile X-ray detector 110 is calculated from the distance and orientation information gathered from the passive markers 200 using the camera and represented as a 6 DOF (degrees of freedom) pose information on the mobile X-ray detector 110. Depth measures may also be used.

The image processor 171 is configured to determine the pose or part of the pose of the detector 110. For example, the image processor 171 is configured to determine a position, orientation, or position and orientation of the detector 110 in 3D space relative to the X-ray source 122 based on markers 200 shown by the camera 130 and markers 200 not shown by the camera 130. The patient 500 and/or other object may occlude or block some markers 200 from being seen by the camera 130. In the example show in FIG. 1A, the legs of the patient 500 obstruct one or more (e.g., over half) of the markers 200 as viewed by the camera 130.

The markers not shown by the camera 130 are located by a machine-learned network applied by the image processor 171. The image processor 171 is configured to apply a machine-learned network or model to an image from the camera 130. In response, the machine-learned network or model outputs the locations of markers 200 not shown by the camera 130. The markers 200 visible in the image may be located using a different process or are also located by the application of the machine-learned network or model.

The application of the machine-learned network or model is described below as part of the method of FIG. 3. In other embodiments, the image processor 171 performs other acts using a machine-learned network or model to locate the markers 200.

Figure 3:
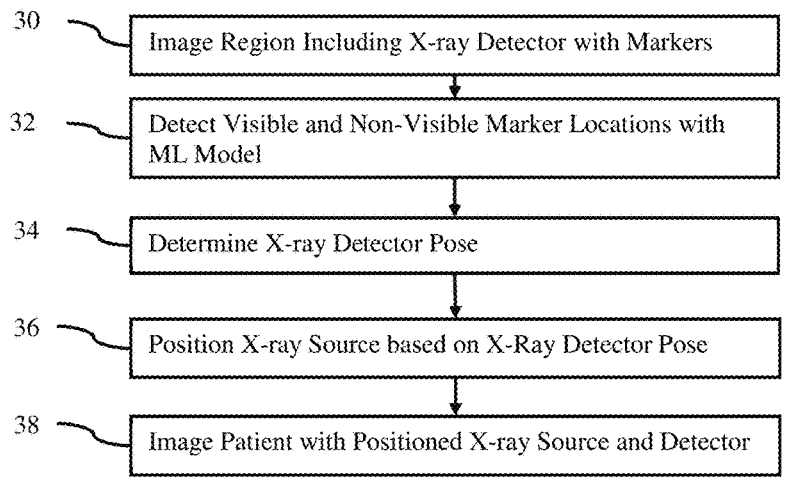
FIG. 3 is a flow chart diagram of one embodiment of a method for estimating X-ray detector pose with a machine-learned model.

FIG. 3 shows one embodiment of estimating X-ray detector pose. The method includes acts for locating markers on an X-ray detector using a machine-learned model. The locations of both visible and occluded or other non-visible markers are determined by application of a captured image to the machine-learned model.

The acts are provided in the orders shown (e.g., top to bottom or numerical), but other orders may be provided. Additional, different or fewer acts may be provided. For example, acts 34, 36, and 38 are not provided in a method to locate the markers. As another example, acts 36 and 38 are not provided in a method to determine pose. In yet other examples, acts for positioning the detector, positioning a patient, configuring the X-ray system, and/or acts using output X-ray images are provided.

In act 30, the camera images a region including the detector with markers and the patient. The region may be imaged with the detector and without the patient. The patient and/or another object may intervene between the camera and one or more (e.g., at least some) of the markers on the detector. One or more parts of the detector, including one or more markers, are visible from the camera.

The imaging captures one or more images of the X-ray detector. An IR or visual spectrum image of the detector, as occluded, is captured. A sequence of such images or just one image once the detector and patient are positioned is captured.

The camera is fixedly connected with the X-ray tube. The captured image is from a perspective similar to the X-ray tube, such as viewing in a same direction with no or little (e.g., 10 cm or less) offset from the X-ray tube. In other embodiments, the camera is not connected with the X-ray tube and/or is spaced from the X-ray tube. Calibration, measurement, or input are used to provide the spatial relationship of the camera to the X-ray tube at the time of image capture.

The field of view for the camera is at least the same size as the area of the X-ray detector, but may be larger or smaller so that at least part of the X-ray detector is captured by the camera. The camera may have a minimum distance to the detector and/or may be positioned to more likely capture the detector. Once or as currently positioned, the field of view of the camera and the resulting area represented by the captured image includes part or all of the detector. The captured image may be padded, such as adding zero, gray, or other pixel values to increase the area represented. The padding may be by extrapolation or adding a pattern, copies of the image, or other data. In one approach, zero padding is applied to make the captured image 9 times larger, such as adding zero padding in areas to each side and diagonal equal to the area of the captured image (left, right, top, bottom, and at the corners or 3×3 grid with the center area being the captured image and the other areas being processor-added padding). The padding makes it more likely that the entire X-ray detector would be within the area represented in the padded image. The entire detector is more likely in the virtual field of view even if the X-ray detector is partially outside the field of view from the captured image (i.e., of the camera).

In one embodiment, the camera field of view extends over an entirety of the patient bed of the X-ray system. A wide-angle lens and/or the camera being positioned further away from the bed provides this field of view. Alternatively, the camera is moved to different locations to stitch together an image from multiple captures to form the image with the larger field of view. In other embodiments, a smaller field of view is provided.

Figure 4:
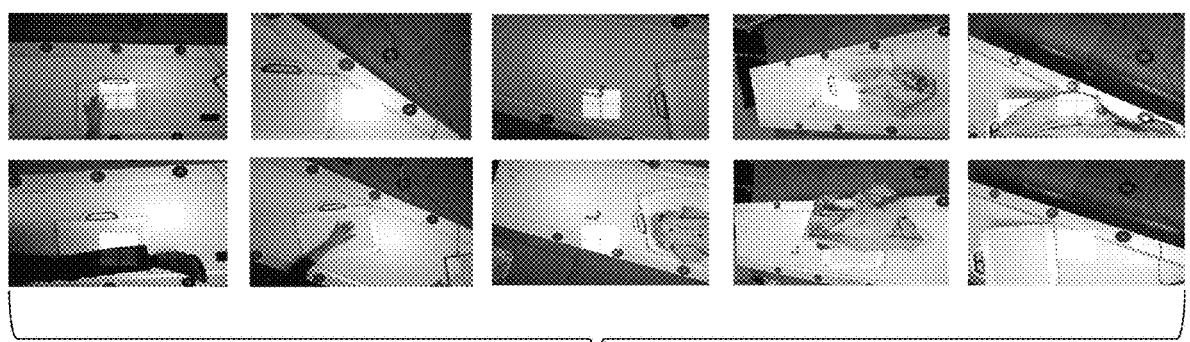
FIG. 4 shows example camera images with occlusion of markers and non-visible markers on an X-ray detector.

The captured image does not show one or more markers due to an intervening object or being out of the field of view. FIG. 4 shows ten example optical images with different sources of occlusion. The occlusion may be due to the patient, clothing, and/or another object. The occlusion may be due to positioning where part of the detector extends beyond the field of view. The pose of the camera with respect to the detector may result in more or less occlusion of markers in the image.

In act 32 of FIG. 3, the image processor identifies locations of visible and occluded markers on the X-ray detector from the captured image. The marker locations are identified by a machine-learned detector. In response to input of the captured image, the machine-learned detector outputs locations of markers including both visible markers and markers not visible (i.e., not shown) in the captured image. For example, the machine-learned model identifies locations of the markers including the markers for which the patient is intervening from the imaging by the camera. In other embodiments, the machine-learned detector outputs the pose of the detector instead of or in addition to the locations of markers.

The machine-learned detector is trained to output the locations given an input image with or without depth information. The training data includes input sample images and corresponding ground truth outputs. Images, including with non-visible markers, and the locations of the markers, including the non-visible markers, are provided as training data.

Figure 5:
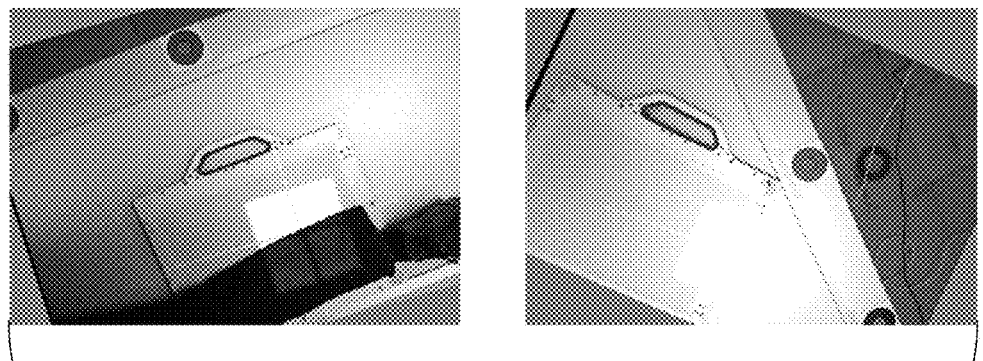
FIG. 5 shows example generation of additional training images.

In one embodiment, a training dataset has 1117 images with ground truth marker locations and/or camera pose and detector pose. 695 images are used for training and 422 for evaluation. Other numbers of images and/or separations for training and evaluation may be used. FIG. 4 shows ten images of the training data where the images corresponding to different detector poses, tube poses, and/or obstructions. To create more samples for training, copies of the 695 images may be altered to form any number of additional images. FIG. 5 shows two images with different scale, rotation, and/or cropping as compared to the source images from FIG. 4. Each or some training images are randomly rotated for 0 to 359 degree followed by a random scaling up (e.g., 1 to 1.15 ratio) and/or random cropping. Other augmentation for training data may be used.

In one embodiment, the ground truth is marker location by pixel to learnt to output a heatmap. Each individual marker is represented as a heatmap in an individual output channel of the machine-learned architecture so that the classification of each marker is implicitly done during marker detection. With 28 markers, the output from the machine-learned detector and the ground truth provided for training is a H×W×28 heatmap where H is height and W is width for the image. In alternative embodiments, a point, line, area, or other designation is used instead of a heatmap for the output and/or the ground truth are heatmaps.

The architecture to be machine trained is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning.

The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

Deep learning may be used. Rather than pre-programming the features and trying to relate the features to attributes, the deep architecture is defined to learn the features at different levels of abstraction based on an input image or scan data with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction. Different units are provided for learning different features.

In one embodiment, the architecture is a neural network. Deep learning is applied to train features to be extracted from the images and the detection to be performed from the features. In one embodiment, the machine-learned network is a fully convolutional network, such as a convolutional-to-transposed-convolutional network. The machine-learned network may be a U-net encoder-decoder. Multiple levels of feature compression or abstraction are provided, such as four. The encoder segment has a plurality of convolutional layers with increasing feature compression or abstraction, and the decoder segment has a plurality of transposed-convolutional layers with decreasing feature compression or abstraction. Skip connections may or may not be provided. Other image-to-image architectures may be used, such as a generative adversarial network where the discriminator is used for training and not for application.

Figure 6:
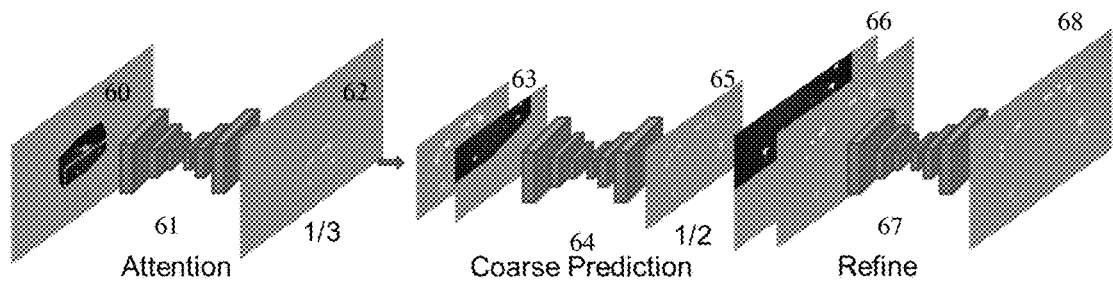
FIG. 6 illustrates an example network architecture for the machine-learned model.

The architecture may include a hierarchy or sequence of two or more networks or models. FIG. 6 shows an example with three networks—attention network 61, coarse prediction network 64 and refining prediction network 67. The markers on the detector are not always visible due to occlusion and being out of the field of view. The architecture implements a padding-and-attention marker detection and prediction pipeline to robustly detect all markers. In other embodiments, the course network 64 and refining prediction network 67 are combined to be one network. In other embodiments, the coarse network 61, coarse prediction network 64, and refining prediction network 67 are combined to be one network directly working on the input with original resolution without any resizing.

In the embodiment of FIG. 6, the attention network 61 is trained to localize the X-ray detector in the image 60. The attention network 61 is an image-to-image network, such as a U-net. In one embodiment, the attention network 61 is a U-Net with 4 stride-2 convolutions for encoder and decoder.

The original IR or other image 60 is padded to ensure the whole detector is likely to be represented in a single image plane. The padding may be by extrapolation from the capture image 60 and/or by zero padding. The field of view may not include the entire detector. In one embodiment, the padding fills in uniform values of zero. Since the detector is assumed to be partially inside field of view of the camera and the detector is not larger than the original image size, then by adding the zeros with the same size of image on both horizontally and vertically (640×480→1920×1440), the field of view is virtually enlarged and the whole detector would be inside the padded image even if not captured in the padded areas.

The padded image 60 is resized (e.g., sampled or down-sampled) from 1920×1440 to 640×480, but no resizing and/or other sizes or resolutions may be used. The attention network 61 receives the image 60 and estimates the center of the detector or a region including the detector. A heatmap 62 of the detector, region designator (e.g., rectangle corresponding to the detector or a part of the image 60 surrounding the detector), or center of the detector (e.g., as a heatmap) is output. The attention network 61 is trained to locate the detector in the field of view of the camera.

A 640×480 or another sized ROI is cropped around the detected detector center or for the detected region including the detector from the original (e.g., 1920×1440) padded image 60. The 640×480 ROI 63 is then resized to 320×240 or other scale to obtain a marker prediction at coarse level. This cropped and resized image 63 is to be input to the coarse prediction network 64. Other inputs may be used, such as an image cropped without resizing.

The coarse prediction network 64 is trained to identify the locations of the markers, including markers not visible in the image 60. The visible and not visible markers are to be located or output. The coarse prediction network 64 is an image-to-image network, such as a U-net. In one embodiment, the attention network 61 is a U-Net with 7 stride-2 convolutions for encoder and decoder.

The coarse prediction network 64 is trained to output marker positions at the coarse resolution. The output is a location for each marker. An orientation of each marker may be output. In another embodiment, the output is a heatmap indicating locations for each marker as probabilities.

The output is up-sampled to a resolution of the original image 60 or other resolution. This up-sampled heat map or coarse marker locations 66 are input to the refine prediction network 67. The cropped region of the original image 60 may be input with the up-sampled output. Alternatively, the original image 60 is input with an overlay based on the coarse marker locations from the coarse prediction network 64.

The refine prediction network 67 is trained to identify the locations of the markers, including markers not visible in the image 60. The visible and not visible markers are located or output at a resolution of the original image 60 or other resolution. The refine prediction network 67 is an image-to-image network, such as a U-net. In one embodiment, the attention network 61 is a U-Net with 5 stride-2 convolutions for encoder and decoder.

The refine prediction network 67 is trained to output marker positions at the desired resolution. The coarse predictions of location are refined. The output is a location or position for each marker. An orientation of each marker may be output. In another embodiment, the output is a heatmap 68 indicating locations for each marker as probabilities. The output is an identification of the locations (e.g., position and/or orientation) of the markers, including both visible and non-visible markers.

In the embodiment of FIG. 6, the convolution layers use a same 3×3 kernel size for all layers of all networks 61, 64, 67. The 3×3 region represents a different size or number of pixels relative to the original image in any down-sampled or different resolutions. In alternative embodiments, different layers and/or networks have different sized and/or shaped kernels for convolution. In yet other alternatives, different network architectures are used, such as one image-to-image or another neural network to receive input of the image 60 and output the locations of the markers. In other embodiments, another network is provided to use the marker locations to output pose of the detector.

Once the architecture is defined, a machine (e.g., image processor, workstation, computer, or server) trains the network arrangement with the training data having ground truth. The neural network or networks are trained using the sample images and the ground truth. Machine learning is performed to train the various units using of the defined architecture. The features (e.g., convolution kernels, transposed-convolution kernels, weights, and max pooling connections) that are determinative or map to the ground truth are learned. The features providing the desired result or detection of the object are learned. Alternatively or additionally, the relationship of input features (e.g., Haar wavelets, gradients, centerlines, segmentation, or other derivations from the anatomy or tissue images) to the ground truth are learned. Rather than or in addition to learning filter kernels for convolution, the relationship of input feature vectors from the image to output marker locations or detector pose is learned.

The network is trained end-to-end. The results relative to the ground truth and the error are back-projected to learn the features that work best. In one embodiment, a L2-norm loss is used to optimize the network. Other error functions may be used. In one embodiment, the values of variables of the network are randomly initialized, but another initialization may be used. End-to-end training is performed, but one or more features may be set. Batch normalization, dropout, and data augmentation are not used, but may be. The optimization is with the RMSprop optimizer, but other optimization functions (e.g., Adam, SGD, etc.) may be used. During the optimization, the different distinguishing features are learned. The features providing an indication of location input image are learned.

In other embodiments, one or more of the networks 61, 64, 67 are pre-trained. For example, the attention network 61 is pretrained using image samples with ground truths for detector region or center. The pre-trained attention network 61 is then trained end-to-end with the other networks 64, 67 using ground truth and corresponding loss for marker locations. Multi-task learning may be used where a loss is provided for each of the networks in training.

The model or detector learns to output the locations of visible and/or non-visible markers given an input image. Once trained, the model may be applied to locate markers in the image and/or determine the pose of the detector from the image. The trained network is configured by the machine training to generate locations or a heatmap of locations given a previously unseen input image.

In act 34 of FIG. 3, the image processor determines the X-ray detector pose of the X-ray detector. The pose is determined as an orientation, position or orientation and position. The pose is in two or three dimensions. For example, the pose is a 3D pose relative to the camera.

Part of the pose may be based on depths measured by the camera. The depths of the visible markers may be used to determine the pose, as an initial or starting pose, pose in a sub-set of the degrees of freedom of the detector relative to the camera. Alternatively, the depths are used as input to the machine-learned model for locating markers or are not used.

The pose is determined using the locations of the visible and non-visible (e.g., occluded or other out-of-view) markers. Where a heatmap is output, the location or locations corresponding to a greatest probability for each marker are selected as the location of the marker.

The distribution of markers indicates the pose. The orientation of one or more markers, orientation of markers relative to each other, the distance between markers, the alignment of markers relative to the camera field of view, and/or other geometrical relationship of or between markers indicates the pose.

In one embodiment, the image processor determines the X-ray detector pose with homography. The detected locations of the markers are used to compute a homography to warp a pre-defined template of the markers to a source image (e.g., output heatmap). The warping error or matching is used to indicate the pose of the detector. Alternatively, the pose is output by the machine-learned model based on estimation from the locations provided within the machine-learned model.

In act 36, the controller controls the robot system to position the X-ray tube based on the X-ray detector pose. A robotic arm positions the X-ray source relative to the detector pose (position and/or orientation). Alternatively, the X-ray tube is manually positioned but with guidance based on the detected pose of the detector (e.g., displaying graphics on the direction and magnitude of movement to align the X-ray tube with the detector).

Once the pose of the mobile X-ray detector is estimated in the form of the 6 degrees of freedom in the camera coordinate system, that location information is transformed into a location in the X-ray base coordinate system. Then, inverse kinematics may be applied to derive the optimal X-ray control parameters (by converting the location in the X-ray base coordinate system to a position in the X-ray source coordinate system) so that the positionable X-ray source is moved into a position that is in alignment with the mobile X-ray detector (e.g., orthogonal to the detector at a desired distance from the detector). The robot system moves the X-ray tube into the aligned position.

In act 38, the X-ray system images the patient. The patient is imaged with the X-ray tube positioned relative to the X-ray detector. Once positioned, the X-ray tube generates X-rays. The X-rays passing through the patient are detected by the detector.

Figure 7:
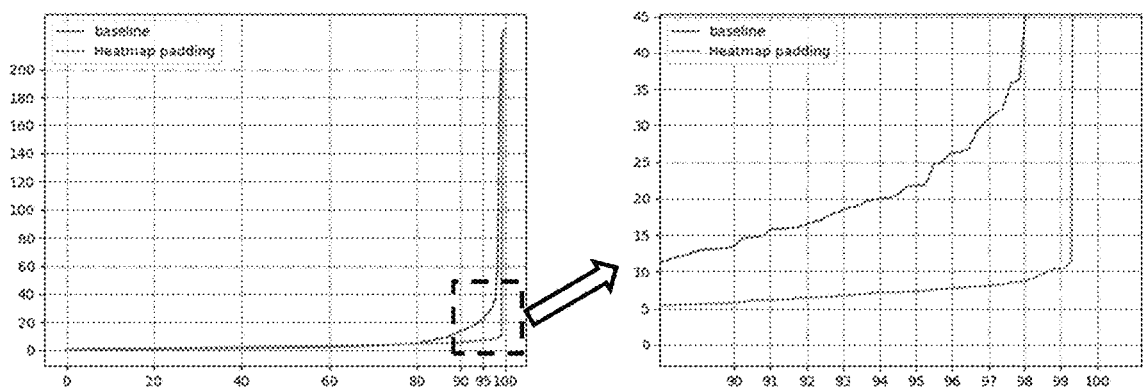
FIG. 7 shows an example graph of accuracy in pose estimation and an expanded view of part of the graph.

FIG. 7 compares using the machine-learned model of FIG. 6 to regress both visible and not visible markers and using a baseline machine-learned model (e.g., single U-net without attention and coarse-to-fine) to regress just the visible markers in detector pose determination. The machine-learned model of FIG. 6 is trained for detecting visible and not visible markers. Nomography is applied to the regressed marker locations in both the baseline and non-visible model to determine detector pose. FIG. 7 shows the sorted root mean square error (y-axis) in the detector position with the baseline regression of only visible markers and with regression of visible and non-visible markers. The x-axis is the error at different percentiles of number of cases. At 90-99% of cases, regression including the non-visible markers provides less error, such as half the error.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for estimating X-ray detector pose, the method comprising:
capturing an image of the X-ray detector;
identifying locations of visible and non-visible markers on the X-ray detector from the image, the identifying being by a machine-learned detector;
determining the X-ray detector pose of the X-ray detector from the locations of the visible and non-visible markers;
positioning an X-ray tube based on the X-ray detector pose; and
X-ray imaging a patient with the X-ray tube as positioned and the X-ray detector,
wherein identifying comprises identifying with the machine-learned detector comprising a sequence of two or more networks, and
wherein identifying comprises identifying with a first of the two or more networks trained to localize the X-ray detector in the image and a second of the two or more networks trained to locate the visible and non-visible markers in response to the localization output by the first of the two or more networks.

2. The method of claim 1 wherein capturing comprises capturing the image as an infrared image.

3. The method of claim 1 wherein capturing comprises capturing the image with a camera fixedly connected and moveable with the X-ray tube.

4. The method of claim 1 wherein capturing comprises capturing the image with a field of view at least an area of the X-ray detector, and wherein identifying comprises identifying from the image comprising padding data.

5. The method of claim 1 wherein identifying comprises identifying with the machine-learned detector comprises a deep learned neural network.

6. The method of claim 1 wherein identifying comprises identifying with a third of the two or more networks trained to refine positions of the visible and non-visible markers output by the second of the two or more networks, the refined positions comprising the identified locations.

7. The method of claim 1 wherein identifying comprises identifying with the second of the two or more networks trained to locate in response to an input of the image cropped based on the localization output.

8. The method of claim 1 wherein identifying comprises generating a heatmap of the locations.

9. The method of claim 1 wherein the image does not show the non-visible markers due to an intervening object, and wherein identifying comprises identifying the locations of the non-visible markers not shown by the image.

10. The method of claim 1 wherein determining comprises determining the X-ray detector pose with homography, the X-ray detector pose including a position and orientation in three dimensions.

11. An X-ray imaging system comprising:
an X-ray source connected to a movable arm;
a camera connected to the X-ray source or moveable arm to be movable with the X-ray source;
a detector moveable independent of the movable arm; and
an image processor configured to determine a position, orientation, or position and orientation of the detector relative to the X-ray source based on markers shown by the camera and markers not shown by the camera, the markers not shown by the camera located by a machine-learned network,
wherein the image processor is configured to apply the machine-learned network to an image from the camera, the machine-learned network outputting the markers not shown by the camera in response to the application.

12. The X-ray imaging system of claim 11 wherein the moveable arm comprises a robotic arm and wherein the detector comprises a flat panel detector.

13. The X-ray imaging system of claim 11 wherein the camera comprises an infrared camera.

14. The X-ray imaging system of claim 11 further comprising a display configured to display an X-ray image of the patient based on positioning of the X-ray source relative to the position, orientation, or position and orientation determined by the image processor.

15. A method for locating markers on an X-ray detector, the method comprising:
imaging a region including a detector with markers and a patient with a camera, the patient intervening between the camera and at least some of the markers; and
determining, by a machine-learned model and from the imaging, locations of the markers including the at least some of the markers for which the patient is intervening,
wherein the region comprises a field of view of the camera at least 5 times an area of the detector, wherein determining comprises determining by the machine-learned model comprising a machine-learned network including a first image-to-image network trained to locate the detector in the field of view of the camera and a second image-to-image network trained to determine the locations from the imaging cropped based on the located detector from the first image-to-image network.

16. The method of claim 15 wherein imaging comprises imaging with infrared and wherein the markers are infrared markers, and further comprising determining a position and orientation of the detector based on the locations and positioning an X-ray source with a robotic arm based on the position and orientation of the detector.

* * * * *